United States Patent [19]
Alexander et al.

[11] Patent Number: 5,227,373
[45] Date of Patent: Jul. 13, 1993

[54] LYOPHILIZED IFOSFAMIDE COMPOSITIONS

[75] Inventors: Robert L. Alexander, Evansville; Robert J. Behme, Newburgh; Joseph A. Scott, Evansville; Dana Brooke, Evansville, all of Ind.

[73] Assignee: Bristol-Myers Squibb Co., New York, N.Y.

[21] Appl. No.: 781,436

[22] Filed: Oct. 23, 1991

[51] Int. Cl.$^5$ .............. A61K 31/66; A61K 31/17; A61K 31/095
[52] U.S. Cl. .................... 514/110; 514/588; 514/706; 514/970
[58] Field of Search ........... 514/110, 588, 706, 970; 558/81

[56] References Cited

U.S. PATENT DOCUMENTS

| | | | |
|---|---|---|---|
| 3,732,340 | 5/1973 | Arnold et al. | 558/81 |
| 4,537,883 | 8/1985 | Alexander et al. | 514/110 |
| 4,716,242 | 12/1987 | Engel et al. | 558/81 |
| 4,882,452 | 11/1989 | Engel et al. | 558/81 |
| 4,952,575 | 8/1990 | Sauerbier et al. | 514/110 |
| 4,959,215 | 9/1990 | Sauerbier et al. | 424/422 |
| 5,036,060 | 7/1991 | Alam et al. | 514/110 |

FOREIGN PATENT DOCUMENTS

0265812 5/1988 European Pat. Off.

Primary Examiner—Frederick E. Waddell
Assistant Examiner—K. Weddington
Attorney, Agent, or Firm—Richard P. Ryan

[57] ABSTRACT

Improved lyophilizate compositions of ifosfamide comprising urea as the primary excipient and, optionally, mesna, are produced in a modified freeze-drying process to give products with increased heat stability and extended shelf storage life.

13 Claims, No Drawings

LYOPHILIZED IFOSFAMIDE COMPOSITIONS

FIELD OF THE INVENTION

The present invention comprises the discovery of lyophilized ifosfamide compositions having improved properties over previously disclosed pharmaceutical compositions and lyophilizates.

BACKGROUND OF THE INVENTION

Ifosfamide, chemically 3-(2-chloroethyl)-2-(chloroethylamino)-tetrahydro-2H-1,3,2-oxazaphosphorin-2-oxide, is a member of the oxazaphosphorin class of alkylating cytostatic antitumor agents. Ifosfamide was included in a series of cytostatic compounds disclosed and claimed by Arnold et al., in U.S. Pat. No. 3,732,340 which issued May 8, 1973.

Ifosfamide is soluble in water slightly in excess of 10 percent by weight. The aqueous solution however remains stable for only a few days when stored at room temperature. The anhydrous form of ifosfamide is a white crystalline powder which melts in the range 48° to 51° C. Because the anhydrous solid form begins to sinter below its melting point, as well as being hygroscopic, the drug should be protected from heat and humidity. Additional problems have been encountered due to other characteristics of the ifosfamide drug substance, and inventive pharmaceutical compounding and processing improvements have been disclosed.

U.S. Pat. No. 4,882,452 issued Nov. 21, 1989 to Engel, et al., claims particularly characterized crystalline ifosfamide and processes for its preparation. This form of ifosfamide had superior dry flow properties which improved vial-filling processes for the anhydrous form of the drug.

In U.S. Pat. No. 4,952,572, Sauerbier, et al. disclosed sealed vials of concentrated non-aqueous solutions of ifosfamide for further dilution with water for parenteral administration.

Due to problems such as short shelf-storage of these solid and solution forms of ifosfamide, lyophilized formulations have been disclosed and claimed as having improved storage life as well as being particularly well suited for the preparation of injectable solutions of ifosfamide.

Sauerbier, et al., disclosed lyophilized ifosfamide-hexitol compositions in European Patent Application EP 265,812, published May 4, 1988. The lyophilizates were claimed to be superior to dry crystalline ifosfamide for use in filled vials for reconstitution. Mannitol was the preferred hexitol component in the lyophilizate composition. Sauerbier, et al., have also disclosed and claimed in U.S. Pat. No. 4,959,215, lyophilized ifosfamide-hexitol compositions additionally containing mesna, which functions as a uroprotectant. Again the preferred hexitol was mannitol.

Earlier, Alexander, et al., in U.S. Pat. No. 4,537,883 had disclosed and claimed hydrated mannitol lyophilizates comprising the oxazaphosphorin, cyclophosphamide. Urea was disclosed as an unsuitable primary excipient in those compositions. Recently Alam, et al., in U.S. Pat. No. 5,036,060 disclosed and claimed a mannitol-free lyophilized formulation of cyclophosphamide in which sodium chloride served as the primary excipient.

The lyophilizate compositions of the present invention which comprise ifosfamide; urea; and optionally, mesna; exhibit improved stability with superior dissolution characteristics and enhanced appearance in comparison with dry ifosfamide powder, nonaqueous concentrated solutions or previous lyophilizate compositions of ifosfamide. It was unexpected that urea as a primary excipient would impart superior stability for an ifosfamide lyophilizate compared to other excipients, especially hexitols. Alexander, et al. in U.S. Pat. No. 4,537,883 reported that mannitol was superior to urea as well as most other pharmaceutical excipients as the primary excipient in cyclophosphamide lyophilizate compositions. Of greater relevance, Sauerbier, et al. disclosed the preference of hexitols, especially mannitol, as the primary excipient in ifosfamide lyophilizate compositions.

SUMMARY OF THE INVENTION

This invention concerns improved solid pharmaceutical compositions containing ifosfamide. These improved compositions are lyophilizates comprising urea as the primary excipient. The uroprotector, mesna, may also be incorporated in the improved lyophilizate. These improved lyophilizate compositions possess greater thermal stability, superior dissolution characteristics and enhanced appearance on storage than previously disclosed ifosfamide compositions, including other lyophilizate compositions especially at higher temperatures. The improvement of lyophilizate compositions using urea as the primary excipient is unexpected, particularly in view of prior art with ifosfamide and our earlier work with the oxazaphosphorin cyclophosphamide. A process for preparing the improved ifosfamide-urea lyophilizates was developed to maximize chemical stability of lyophilized ifosfamide.

DETAILED DESCRIPTION OF THE INVENTION

The therapeutically active component of this invention, ifosfamide, is a well known and widely used anticancer drug. While ifosfamide is a valuable agent in the cancer chemotherapy area, nonetheless certain problems have been experienced due to ifosfamide's physico-chemical properties. In particular, ifosfamide's hygroscopicity and deliquescence at high humidity create problems in processing, shipping, storage, and reconstitution. For each of these stages ifosfamide must be stored at room temperature or lower and must be processed at low relative humidity. Ifosfamide solutions are not suitably stable primarily due to solvolytic processes which degrade the ifosfamide molecule. The use of non-aqueous/non-hydrolytic solvents for solution products is complicated by their presence in the final parenteral solution for administration and may also present safety issues.

The introduction of pharmaceutical lyophilizate compositions of oxazaphosphorins in ampuls or sealed vials represented an improvement over prior pharmaceutical compositions of these anticancer agents. Incorporation of lyophilization processes allows facile production of solid oxazaphosphorin compositions in vials for reconstitution as a sterile solution. The lyophilizate compositions also demonstrate better storage stability and dissolution characteristics than previous solid dosage formulations. The lyophilizate compositions of the present invention demonstrate unexpected improvements in physical and chemical stability at elevated temperature and shelf-life over previous lyophilizate formulations of ifosfamide and formulations combining ifosfamide and mesna.

The present invention has resulted from work undertaken to ascertain if physical properties, especially shelf-storage and temperature stability, could be improved in a lyophilized ifosfamide pharmaceutical composition. The initial stage of this research involved evaluation of the suitability of lyophilizate cakes formed by freeze-drying various ifosfamide-excipient compositions. In making these evaluations, certain characteristics of the lyophilizate cakes were observed including original shape, shrinkage or meltback, coloration, homogeneity, morphology, firmness and crystallinity. The dissolution characteristics of prototypes were then determined and these included rate of dissolution, completeness of dissolution, and characterization of the resultant solution; e.g. clarity and color.

The second stage of the research involved short term accelerated stability studies of compositions selected on the basis of their performance in the first stage of research. Excipients that were tested but not advanced to stage two evaluation included lactose; polyvinylpyrrolidone (PVP); dextrose; sodium bicarbonate; sodium carbonate; and tartaric acid. Lyophilizate compositions having mannitol, glycine, or urea as primary excipients were selected for the stage two stability testing. Lyophilizate compositions with mannitol or glycine as the primary excipient yellowed and decreased in potency during short term stability studies carried out at 40° C. In studies conducted at ambient room temperature (24°–27° C.), chemical and physical stability for the mannitol and glycine lyophilizate compositions was maintained for about 39 weeks. After 1 year storage lyophilizate compositions with mannitol or glycine were yellowed. Lyophilizate compositions with urea as the primary excipient showed no yellowing or significant potency loss during storage under all conditions studied.

The improved stability of urea-ifosfamide lyophilizates over those containing mannitol or glycine was apparent when it was unexpectedly discovered that these lyophilizates could also be stored at 60° C. for 3 months without significant change in appearance or potency. This was especially surprising since 60° C. is 10° C. higher than the melting point of ifosfamide. In contrast, the mannitol and glycine lyophilizate compositions showed significant physical changes and potency loss at 40° C., 10° C. below the melting point of ifosfamide. By way of comparison, preferred lyophilizate compositions of the present invention which contain a ratio of ifosamide to urea approaching equal parts by weight were essentially unchanged after storage for at least one year at 35° and 26 weeks at 40° C.

The improved ifosfamide lyophilizate compositions of the present invention exhibit improved thermal and storage stability while maintaining superior dissolution characteristics without changes in appearance. In general these improved compositions comprise from about 0.3 to 5 parts by weight of urea to each part by weight of ifosfamide. Preferred compositions comprise about 0.8 to 15 parts by weight of urea to each part by weight of ifosfamide and most preferred compositions are comprised of approximately equal parts by weight of urea and ifosfamide.

These improved urea-ifosfamide lyophilizate compositions may be modified by incorporation of minor amounts of other excipient materials, other conventional pharmaceutical additives, or by the incorporation of uroprotecting amounts of the detoxifying agent mesna. Chemically, mesna is sodium 2-mercaptoethanesulfonate. In this regard lyophilized compositions comprising from about 0.1 to 1 part by weight of mesna and from about 0.3 to 5 parts by weight of urea to each part by weight of ifosfamide are to be considered part of the instant invention.

Another aspect of the present invention concerns the use of a slow freeze-drying process for preparing the urea-ifosfamide lyophilizate compositions. This process results in minimization of shrinkage of the lyophilizate cake which was previously seen in urea-oxazaphosphorin lyophilizate compositions. The control of shrinkage and absence of yellowing for these improved lyophilizate compositions contribute to the enhanced appearance of the pharmaceutical product. In order to produce these improved urea lyophilizate compositions, it was learned that by controlling both the rate of freezing of the solution prior to vacuumdrying, shrinkage problems previously seen with the urea lyophilizates were minimized. The particular lyophilizate processes used to achieve the enhanced appearance of the urea lyophilizate compositions are set forth suora in the specific examples.

The improved lyophilizate compositions of the present invention are prepared by dissolving ifosfamide and urea; and optionally, lesser amounts of other pharmaceutical excipients and/or mesna; in water of suitable quality. These aqueous solutions will be comprised of 4.0 to 10.0% by weight to water volume of ifosfamide and 1.2 to 20.0% by weight to water volume of urea. From 0.4 to 4.0% by weight to water volume of mesna may be optionally incorporated. In addition, other pharmaceutically useful auxiliary materials, such as excipients, buffers, preservatives and the like; in lesser amounts may be added to the solution and not depart from the present invention. While water is the preferred solvent for the solution, it would be possible to use hydroalcoholic or other pharmaceutically acceptable solvents.

The pre-lyophilization solution is purified in a conventional manner by filtration using microbial retentive filters and nitrogen gas for pre-filter pressure. The filtration-sterilized solution is then aseptically filled into sterile packaging of appropriate size to allow reconstitution with water to give an intended volume of solution of desired ifosfamide concentration for administration. Typically, vials are used and will contain sufficient fill solution to provide 1.0 g or 3.0 g of ifosfamide per vial.

Following the filling operation, the vials, with lyophilization stoppers in the raised position, are loaded into trays and shelf-frozen in the lyophilizer chamber to about −40° C. The frozen solution is then lyophilized in the following manner; initially, the shelf temperature is set at about 0° C. and the vacuum is maintained at about 0.5 torr with the condenser temperature at about −60° C. or lower. After completion of the primary drying (generally, about 24 to 48 hours), the shelf temperature is raised to about 25° to 28° C. and the chamber vacuum is lowered to about 0.1 torr or less. These drying conditions are continued until the residual moisture in the lyophilizate is reduced to a level whereby ifosfamide is chemically stable. Generally, the secondary drying requires an additional 24–36 hours.

The ifosfamide-urea and ifosfamide-urea-mesna lyophilizate compositions typically to be marketed will contain between about 500 mg and 5 g, preferably about 1 g to 3 g of ifosfamide per unit. The amount of mesna contained in a lyophilizate unit dosage form will be about 100 mg to 3 g. Larger sized dosage forms of improved ifosfamide-urea lyophilized compositions are also possible and would be a further embodiment of the present invention. The dosage forms will then comprise an ifosfamide lyophilizate composition as described suora, contained in a suitable container, usually a vial but also an ampoule, syringe, or other container commonly used for packaging; reconstitution; and, optionally, delivery of intravenous or parenteral solutions. By suitable container is meant a container capable of maintaining a sterile environment such as a vial capable of being hermetically sealed by a stopper means. Additionally, suitable container implies appropriateness of size, considering the volume of solution to be held upon reconstitution of the improved ifosfamide lyophilizate composition. While such containers are usually glass, generally type I glass; they may also be of other suitable materials which do not interact with the lyophilizate components. The closure, typically a stopper and preferably a sterile rubber stopper or an equivalent which gives a hermetic seal, will also allow entry for the purpose of introduction of diluent such as sterile water for reconstitution of the ifosfamide solution. Preferred dosage forms containing the improved ifosfamide lyophilizate compositions will be vials from about 10 to 250 ml and preferably about 25 to 100 ml in capacity. It will be recognized that larger or smaller dosage forms may be readily accommodated as part of the present invention.

The ifosfamide-urea and ifosfamide-urea mesna lyophilizate compositions of the present invention are intended to be reconstituted with common diluents, such as Water for Injection, USP, to provide appropriate solutions of ifosfamide and ifosfamide-mesna for parenteral administration, preferably intravenous administration.

Representative vials of ifosfamide lyophilizates have been subjected to stability testing. Samples of the instant improved urea-ifosfamide lyophilizate compositions were compared with lyophilized compositions using glycine or mannitol as primary excipients. The mannitol-ifosfamide compositions represent those taught by Sauerbier, et al., in U.S. Pat. No. 4,959,215. As can be seen in table 1, the urea-ifosfamide lyophilizate compositions represent clear improvement in storage stability over the reference compositions.

TABLE 1

Comparative Storage Stabilities for 1:1 Excipient to Ifosfamide Lyophilizate Compositions With Different Primary Excipients (A = urea; B = glycine; C = mannitol)

| Storage Temperature | Age (Wks) | Cake Appearance A | B | C | Potency (% of Initial) A | B | C |
|---|---|---|---|---|---|---|---|
| 40° C. | 6 | Unchanged | sl. yell. | sl. yell. | 99 | 94 | 93 |
| | 12 | Unchanged | sl. yell. | sl. yell. | 100 | 89 | 88 |
| | 26 | Unchanged | yell. | yell. | 100 | 79 | 78 |
| 35° C. | 6 | Unchanged | Unchan. | Unch. | 100 | 98 | 96 |
| | 12 | Unchanged | sl. yell. | off white | 100 | 94 | 95 |
| | 26 | Unchanged | sl. yell. | sl. yell. | 100 | 90 | 87 |
| | 39 | Unchanged | yell. | yell. | 100 | 82 | 81 |

Batches of the most preferred 1:1 weight ratio of urea to ifosfamide lyophilizate compositions were also tested under more stringent conditions where instability of the reference lyophilizates (having mannitol or glycine as excipients) rendered their inclusion impractical. In these more stringent tests, the lyophilizates were stored for 12 weeks at 60° C. (a temperature which is ten degrees higher than the melting point of ifosfamide). As shown in Table 2, these improved lyophilizate compositions retained over 95% of their initial potency. The lyophilizate cakes remained white and no cake shrinkage was observed under these accelerated conditions.

TABLE 2

Stability Data for Improved Ifosfamide-Urea Lyophilizate Composition Stored at 60° C.

| Age (wks) | Appearance | Potency (% of Initial) | Dissolution Time (Seconds) |
|---|---|---|---|
| 0 | white homogenous cake | 100 | 10-15 |
| 2 | " | 101 | 10-15 |
| 4 | " | 99 | 10-15 |
| 6 | " | 100 | 10-15 |
| 8 | " | 96 | 10-15 |
| 12 | " | 98 | 10-15 |

As can be seen, the objective of the previously described development work was achieved since the improved lyophilizate compositions display superior properties that result in a marked improvement in shelf-storage and heat stability. Even at 60° C., 10° C. above the melting point of ifosfamide, the lyophilizate compositions of the present invention show little or no change in appearance, dissolution rate, and drug potency.

The following examples describe in detail methods for preparation of the improved urea-ifosfamide and urea-ifosfamide-mesna lyophilizate compositions of the present invention. It will be apparent to those skilled in the art that many modifications, both of methods and materials may be practiced without departing from the purpose and intent of the disclosure. From the foregoing disclosure and the following examples, it is believed that one skilled in the art is able to use the present invention to the fullest extent.

DESCRIPTION OF SPECIFIC EMBODIMENTS

EXAMPLE 1

An aqueous solution is typically prepared by dissolving ifosfamide (250 g) and urea (250 g) in 2.5 liters of Water for Injection. Additional Water for Injection is added in order to bring the final volume of solution to 3 liters. The solution is first passed through a sterile prefilter and then a sterile 0.2 micron pore size membrane filter, following which the sterile solution is then aseptically filled into sterile 30 ml glass vials. Each vial is filled with 2.0 ml of solution (containing the equivalent of 1 g of ifosfamide) and then sterile rubber stoppers are aseptically inserted in the lyophilization (raised) position. These vials are placed in suitable lyophilization equipment and cooled (shelf-frozen) to a temperature of about −40° C.

The lyophilizer condenser is then cooled to about −60° C. or lower and the lyophilizer chamber is evacuated to a pressure of about 0.5 torr (range of 0.3 to 0.7). Shelf heat temperature is set at about 0° C. to begin the drying process. Following primary drying of about 24 to 48 hours, the shelf temperature is raised in order to bring the product temperature to near +25° C. Lyophilization is then continued until a final product temperature of about 25° C. to 28° C. and a chamber pressure of not more than 0.2 torr, is reached. The total lyophilization time will vary but depending on the capacity of equipment, will generally be in the range of about 72 to 96 hours. Following completion of the lyophilization process, the vacuum is relieved by the aseptic introduction of sterile air and/or nitrogen. At this point the vials are closed by aseptically seating the lyophilization stoppers into the vials by mechanical collapse of the shelves. Vials are then removed from the lyophilizer and are sealed by applying suitable aluminum seals.

The foregoing example describes the most preferred composition (comprised of approximately equal parts by weight of ifosfamide and urea) and its processing. Other compositions of the invention comprising from about 0.3 to 5 parts by weight of urea to each part by weight of ifosfamide can be processed in a similar manner except that due to solubility limitations, various ratios of drug and urea may require larger fill volumes per container and therefore larger container sizes to provide a lyophilizate comprised of 1 g of ifosfamide.

EXAMPLE 2

A lyophilization product containing 3 g of ifosfamide (comprised of approximately equal parts by weight of ifosfamide and urea) would be made in a similar manner except that since the prelyophilization solution volume would be about 36 ml, the package size (vial size) would be about 60 to 100 ml. In addition, due to the larger volume of solution, the required freezing time may be slightly longer. The lyophilizer conditions are the same as described for Example 1 but the total lyophilization time will generally be in the range of about 96 to 120 hours. Stoppering and vial sealing are identical to the 1 g size.

EXAMPLE 3

The composition described in Examples 1 and 2 may also contain lesser amounts of other pharmaceutically useful auxiliary materials such as buffers, preservatives, small quantities of co-excipients and the like and not depart from the present invention. In addition, the improved lyophilizate compositions of the present invention may also contain from 0.1 to 1.0 parts by weight of mesna to each part by weight of ifosfamide. Processing of a composition containing mesna would be accomplished in an essentially identical manner to that described previously.

What is claimed is:

1. A lyophilizate composition having improved heat stability and shelf-life, the lyophilizate comprising from about 0.3 to 5 parts by weight of urea to each part by weight of ifosfamide.

2. A lyophilizate composition of claim 1 comprising about 0.8 to 1.5 parts by weight of urea to each part by weight of ifosfamide.

3. A lyophilizate composition of claim 1 comprising about 1 part by weight of urea to each part by weight of ifosfamide.

4. A lyophilizate composition of claim 1 further comprising about 0.1 to 1 part by weight of sodium 2-mercaptoethanesulfonate, mesna to each part by weight of ifosfamide.

5. A dosage unit formulation comprising the lyophilizate composition of claim 1 in a container of sufficient size to allow reconstitution with diluent to give an intended solution of desired ifosfamide concentration for administration.

6. The dosage unit formulation of claim 5 wherein the lyophilizate composition comprises approximately 1 g of ifosfamide and 1 g of urea.

7. The dosage unit formulation of claim 6 wherein said composition is reconstituted with 20 ml of diluent, such as Water for Injection to provide solution for administration.

8. The dosage unit formulation of claim 5 wherein the lyophilizate composition comprises approximately 3 g of ifosfamide and 3 g of urea.

9. The dosage unit formulation of claim 8 wherein said composition is reconstituted with 60 ml of diluent, such as Water for Injection, to provide solution for administration.

10. The dosage unit formulation of claim 6 wherein the lyophilizate compositions comprise from about 100 mg to 1 g of mesna to each gram of ifosfamide.

11. The dosage unit formulation of claim 8 wherein the lyophilizate compositions comprise from about 100 mg to 1 g of mesna to each gram of ifosfamide.

12. A process for the preparation of a lyophilizate composition having improved heat stability and shelf-life, which comprises freezing an aqueous solution containing from about 0.3 to 5 parts by weight of an excipient consisting essentially of urea to each part by weight of ifosfamide, to a temperature of about −40° C. and removing both nonadsorptively bound and adsorptively bound water by sublimation at a temperature between about −40° C. and about +28° C. and at a pressure between about 0.7 and 0.1 torr.

13. A process according to claim 12 wherein the aqueous solution to be frozen further comprises from about 0.1 to 1 part by weight of sodium-2-mercaptoethanesulfonate, mesna) to each part by weight of ifosfamide.

* * * * *